United States Patent
Kimura et al.

(10) Patent No.: US 6,759,449 B2
(45) Date of Patent: Jul. 6, 2004

(54) DENTAL ADHESIVE COMPOSITION

(75) Inventors: Mikio Kimura, Ibaraki (JP); Koji Matsushige, Ibaraki (JP); Hideki Kazama, Ibaraki (JP)

(73) Assignees: Tokuyama Dental Corporation, Tokyo (JP); Tokuyama Corporation, Tokuyama (JP)

(*) Notice: Subject to any disclaimer, the term of this patent is extended or adjusted under 35 U.S.C. 154(b) by 168 days.

(21) Appl. No.: 10/181,413

(22) PCT Filed: Nov. 27, 2001

(86) PCT No.: PCT/JP01/10334

§ 371 (c)(1), (2), (4) Date: Jul. 23, 2002

(87) PCT Pub. No.: WO02/43669

PCT Pub. Date: Jun. 6, 2002

(65) Prior Publication Data

US 2003/0050359 A1 Mar. 13, 2003

(30) Foreign Application Priority Data

Nov. 28, 2000 (JP) ........................................ 2000-361150

(51) Int. Cl.⁷ .............................................. A61K 6/083
(52) U.S. Cl. ........................ 523/118; 523/116; 523/223; 433/228.1
(58) Field of Search .................................. 523/116, 118, 523/223; 433/228.1

(56) References Cited

FOREIGN PATENT DOCUMENTS

| EP | 896043 | 2/1999 |
|---|---|---|
| JP | 2000-53727 | 2/2000 |
| JP | 02002370915 | * 12/2002 |

* cited by examiner

Primary Examiner—Peter Szekely
(74) Attorney, Agent, or Firm—Oblon, Spivak, McClelland, Maier & Neustadt, P.C.

(57) ABSTRACT

This invention discloses a dental adhesive composition comprising (A) a polymerizable monomer comprising an acidic-group containing polymerizable monomer such as 11-methacryloyloxy-1,1-undecane dicarboxylic acid, (B) a mixed filler of a spherical filler substantially consisting of a non-crosslinking polymethyl methacrylate and a spherical filler substantially consisting of a non-crosslinking polyethyl methacrylate; and (C) a polymerization initiator; and a dental adhesive kit comprising the above dental adhesive composition in combination with a dental primer comprising (D) an acidic-group containing polymerizable monomer, (E) an aryl borate, (F) an organosulfinic acid salt and (G) water. The dental adhesive composition exhibits good operability and improved adhesion performance.

11 Claims, No Drawings ic # DENTAL ADHESIVE COMPOSITION

FIELD OF THE INVENTION

This invention relates to a dental adhesive composition, as well as a dental adhesive kit consisting of a combination of the dental adhesive composition and a dental primer composition.

DESCRIPTION OF THE PRIOR ART

In the field of dental treatment, a damaged tooth due to caries or an accident must be firmly cemented with a restorative material for the tooth including a crown restorative material made by composite resins, metals and ceramics, and a variety of adhesive compositions have been suggested for such cementing.

Among these adhesive compositions, adhesive resin cements have been widely used because they can firmly cement a metal or ceramic prosthesis with a tooth. An adhesive resin cement essentially consists of a monomer component, a filler component and a polymerization initiator. It is believed that an adhesive resin cement containing a non-crosslinking resin filler (non-crosslinking polymer filler) as a filler component gives a cured resin cement exhibiting higher toughness than an adhesive resin cement comprising a crosslinking resin filler or inorganic filler and is adequately resistant to external stress applied to a prosthesis cemented with a tooth to prevent the prosthesis from being easily detached from the tooth. Known adhesive resin cements comprising a non-crosslinking resin filler (hereinafter, referred to as a resin-filler resin cement) include resin cements comprising tributylboran or its partially oxidized (TBBO) as a polymerization initiator and a non-crosslinking polymethyl methacrylate filler as a non-crosslinking polymer filler.

Although such a resin-filler adhesive resin cement advantageously exhibits higher adhesiveness, it has been indicated that it has the following problems in terms of operability in use. Specifically, the above polymerization initiator used in the resin cement is chemically unstable, so that it must be packed separately from the other components. Furthermore, the non-crosslinking polymer filler and the monomer must be also separately packed for preventing the non-crosslinking polymer filler from being dissolved. Thus, in the resin cement, the polymer filler, the monomer liquid and the polymerization initiator solution must be packed separately from each other, i.e., a three-packet system. When using the resin cement, given amounts of the monomer liquid and the polymerization initiator solution are mixed, and then a given amount of the polymer filler is added. This process is troublesome.

When using the resin cement, the three components can be mixed to rapidly increase a viscosity and thus to reduce a time for applying the mixture to a tooth surface and a crown restorative material (hereinafter, referred to as a "working time" or "operable time"). Higher technique which ensures rapid and firm cementing is, therefore, required for achieving desired adhesive strength using the resin cement. When using the polymerization initiator, it takes a longer time until the resin cement is adequately cured to exhibit desired adhesiveness. There is thus a problem that a desired adhesive strength cannot be achieved if a strong force is applied after cementing a prosthesis on the tooth surface and before completion of curing of the resin cement.

There have been no known resin-filler resin cements which can sufficiently endure severe environmental conditions, i.e., in the mouth, to provide good adhesiveness; have a satisfactory working time and an appropriate curing time; and exhibit improved operability.

SUMMARY OF THE INVENTION

An objective of this invention is to provide a resin-filler resin cement meeting the above requirements.

The above problem in terms of packaging depends on stability of a polymerization initiator used. A curing time basically depends on a combination of a polymerization initiator and a monomer. These problems could be, therefore, solved by employing a stable polymerization initiator and a polymerization initiator-monomer system which can be quickly cured and exhibits higher adhesive ability. Actually, many such initiator-monomer systems have been found for a dental adhesive composition other than a resin-filler resin cement and have been practically used. The above two problems could be, therefore, solved by employing such a well-known monomer-initiator system.

However, a resin-filler resin cement contains a non-crosslinking polymer filler as a constituent. Thus, it is inevitable that on mixing a polymer filler with a monomer in use, expansion or dissolution of the polymer filler leads to increase in a viscosity of the mixture. It can be thus said that the above problem in terms of a working time is inherent to a resin-filler resin cement. Furthermore, a working time may vary significantly depending on a combination of a non-crosslinking polymer filler and a monomer. A working time might be increased by replacing one or both of these components. However, since replacing a monomer may substantially affect, e. g., an adhesive strength, it cannot be easily applied.

We thus considered the problem of a working time as a common problem for a dental adhesive composition comprising a non-crosslinking polymer filler and a monomer rather than that for a resin-filler resin cement alone. We have, therefore, attempted to solve the problem of a working time by first selecting an initiator-monomer system employed in a dental adhesive composition other than the above resin-filler resin cement and next developing a non-crosslinking polymer filler providing a suitable working time when being mixed with the initiator-monomer system.

It is well-known that a working time depends on a shape and a particle size of a non-crosslinking polymer filler. Specifically, a working time tends to be reduced by using an irregular form non-crosslinking polymethyl methacrylate filler as a component of a resin cement while it tends to be increased by using a spherical polymethyl methacrylate filler (Shika Zairyo-Kikai, Vol. 18, No.5, 347–351, 1999). It is also known that by controlling a particle size or particle size and surface roughness of an irregular form non-crosslinking polymethyl methacrylate filler can increase a working time to some extent (Shika Zairyo-Kikai, Vol. 19, No.1, 92–101, 2000 and JP-A 2000-53727). When using such a filler to adjust a working time, a curing time of a resin cement may be increased or an elongation of working time may not be sufficient. The above problem cannot be solved only by optimizing a shape or particle size of a filler.

Under such a situation, we have investigated not only a shape and a particle size of a non-crosslinking polymer filler but also its material quality. We have consequently found that a resin cement can be formulated using a mixture of a non-crosslinking polymethyl methacrylate spherical filler and a non-crosslinking polyethyl methacrylate spherical filler to increase a working time of the resin cement without adversely affecting a curing time or adhesive strength, achieving this invention.

This invention provides a dental adhesive composition comprising (A) a polymerizable monomer comprising an acidic-group containing polymerizable monomer; (B) a spherical filler substantially consisting of a non-crosslinking polymethyl methacrylate and a spherical filler substantially consisting of a non-crosslinking polyethyl methacrylate; and (C) a polymerization initiator.

Because a dental adhesive composition of this invention comprises a non-crosslinking polymer filler as a filler component, it can provide a cured product exhibiting higher toughness than that from a dental adhesive composition comprising a crosslinking filler or inorganic filler. Thus, it can adequately endure a stress applied to a prosthesis while maintaining the property in a conventional resin-filler resin cement that a cemented prosthesis is resistant to detachment. It can provide a higher adhesive strength, gives a shorter time to a proper viscosity, and gives an appropriately long working time of 40 to 150 sec, resulting in good operability. Furthermore, a curing time is as short as 5 min or less, the dental adhesive composition of this invention can be used to ensure firm cementing without patient's burden.

This invention also provides a dental adhesion kit consisting of the above dental adhesive composition of this invention in combination with a dental primer comprising (D) an acidic-group containing polymerizable monomer; (E) an aryl borate; (F) an organosulfinic acid salt; and (G) water.

An infiltration promoter for a dental adhesive composition called as a primer is generally applied to a tooth surface to improve adhesiveness of the dental adhesive composition to the tooth before applying the composition.

The adhesive composition of this invention can provide a good adhesive strength when being combined with the primer comprising the above (D) to (G) as well as (H) a polymerizable monomer other than the acidic-group containing polymerizable monomer and (I) an organic solvent. The kit of this invention can be used to provide a higher adhesive strength to both dental enamel and dentin.

DETAILED DESCRIPTION OF PREFERRED EMBODIMENTS

Dental Adhesive Composition (A) Polymerizable Monomer Comprising an Acidic-group Containing Polymerizable Monomer In a dental adhesive composition according to this invention, a polymerizable monomer used as component (A) must comprise at least one acidic-group containing polymerizable monomer. If component (A) comprises no such acidic-group containing polymerizable monomers, the dental adhesive composition does not exhibit good adhesiveness.

An acidic-group containing polymerizable monomer as used herein means a compound containing at least one group that exhibits acidic property in an aqueous solution and at least one polymerizable unsaturated group in a molecule. Examples of the acidic group include a phosphinico group $\{=P(=O)OH\}$, a phosphono group $\{-P(=O)(OH)_2\}$, a carboxyl group $\{-C(=O)OH\}$, a sulfone group $(SO_3H)$ and an organic group containing an acid anhydride structure $\{-C(=O)-O-C(=O)-\}$. Examples of a polymerizable unsaturated group include acryloyl group, methacryloyl group, acrylamide group, methacrylamide group and styryl group.

Any acidic-group containing polymerizable monomer described above can be used with no limitations, but a compound represented by general formula (1) or (2) is preferable because of its higher adhesive strength to a tooth or base metal.

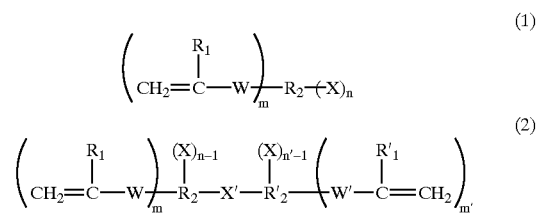

wherein $R_1$ and $R'_1$ independently represent hydrogen atom or methyl group; W and W' independently represent oxycarbonyl group (—COO—), iminocarbonyl group (—CONH—) or phenylene group (—$C_6H_4$—); $R_2$ and $R'_2$ independently represent a single bond or a bivalent to sexavalent $C_1$ to $C_{30}$ organic residue optionally containing an ether bond and/or an ester bond, provided that when W is oxycarbonyl group or iminocarbonyl group, $R_2$ is not a single bond and when W' is oxycarbonyl group or iminocarbonyl group, $R'_2$ is not a single bond; X represents a monovalent acidic group; X' represents a bivalent acidic group; m and m' independently represent an integer of 1 to 4; m+n represents a valency of $R_2$; and m'+n' represents a valency of $R'_2$.

In general formula (1) or (2), X and X' may have any structure as long as it is an acidic group as defined above, but is preferably as illustrated below.

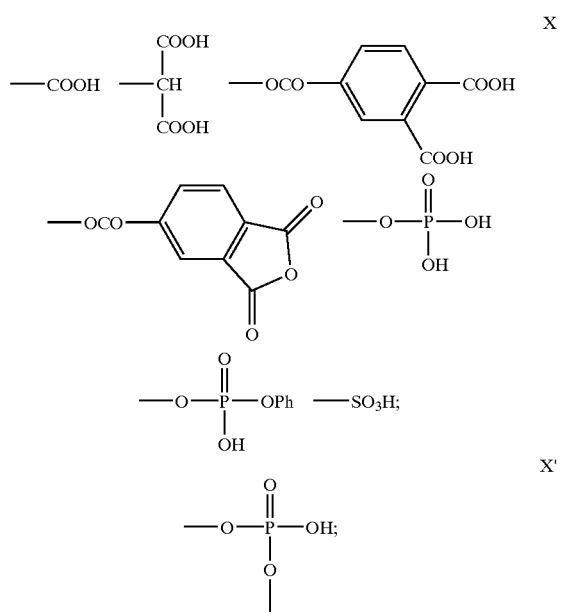

In general formula (1) or (2), $R_2$ may be a single bond or a known bivalent to sexavalent $C_1$ to $C_{30}$ organic residue optionally having an ether bond and/or an ester bond, without limitations. Preferable examples thereof are illustrated below. An expression "$R_2$ is a single bond" herein means that W is directly bound to X via a single bond, and when W is oxycarbonyl group or iminocarbonyl group, $R_2$ is not a single bond. It can be also applied to relationship between $R'_2$ and W'.

-continued
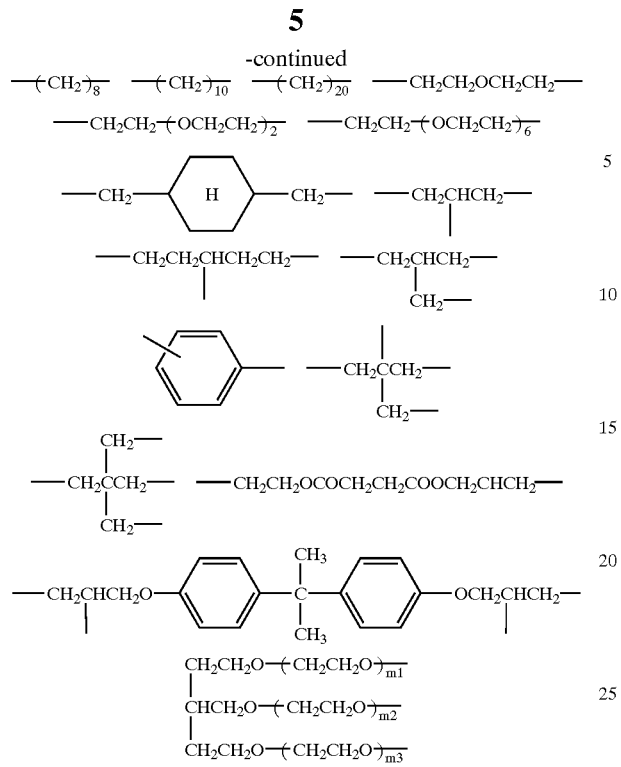
wherein m1, m2 and m3 are independently an integer of 0 to 10 and m1+m2+m3 is one or more.
Preferable examples of an acidic-group containing polymerizable monomer represented by general formula (1) or (2) are as follows:
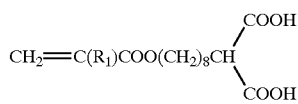
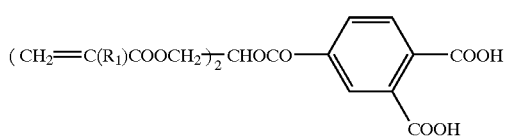
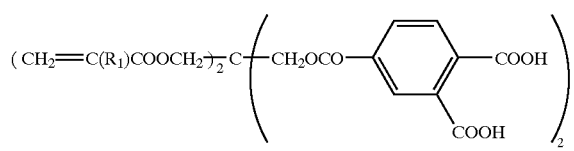
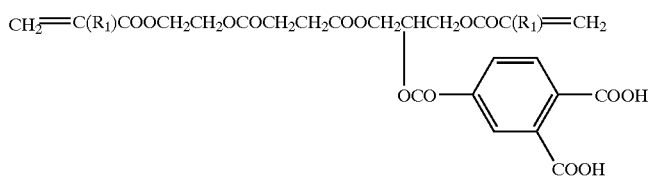
-continued
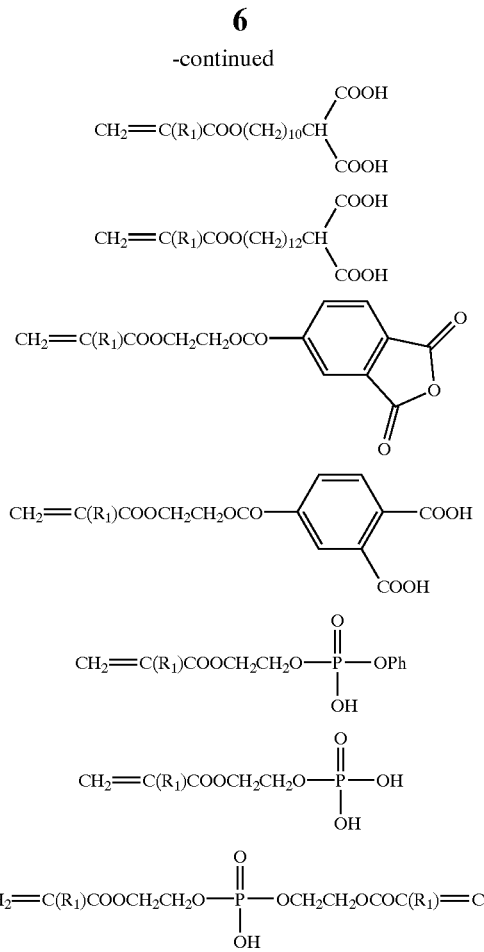
wherein $R_1$ represents hydrogen atom or methyl group;
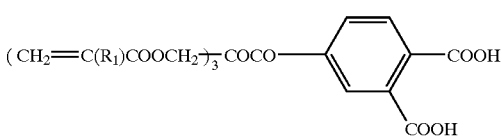

-continued

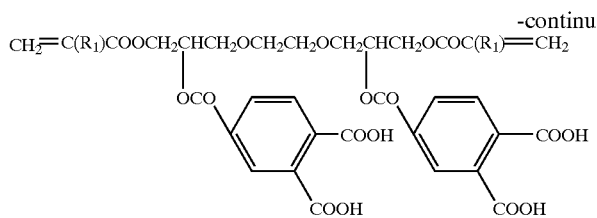

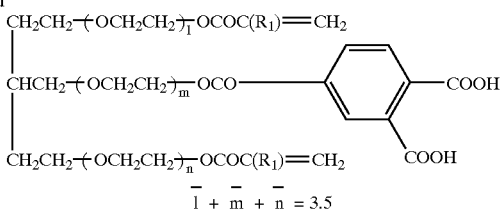

$$\overline{l} + \overline{m} + \overline{n} = 3.5$$

wherein R1 represents hydrogen atom or methyl group; l, m and n in the last compound independently represent an integer of 0 to 2; and the compound is often provided as a mixture of compounds having different l, m and n, in which an average of the sum of l+m+n is 3.5;

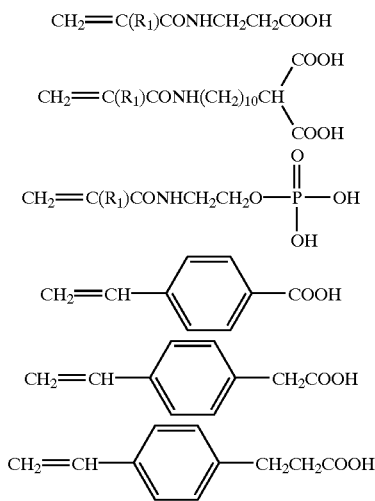

wherein $R_1$ represents hydrogen atom or methyl group;

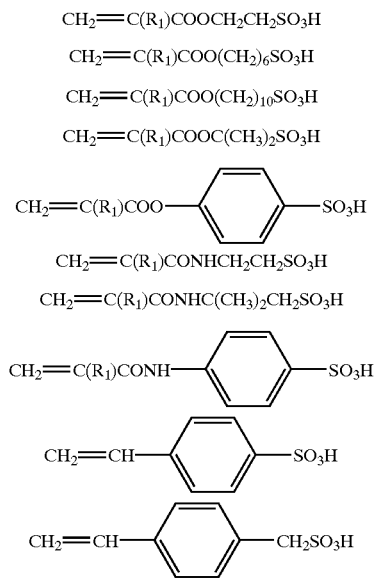

wherein $R_1$ represents hydrogen atom or methyl group.

Additional examples of the acidic-group containing polymerizable monomer include vinylphosphonic acids, acrylic acid, methacrylic acid and vinyl sulfonic acid.

The above acidic-group containing polymerizable monomers may be used alone or in combination of two or more.

Among these acidic-group containing polymerizable monomers illustrated above, particularly preferable compounds are those containing a phosphinico group {=P(=O)OH}, a phosphono group {—P(=O)(OH)$_2$}, a carboxyl group {—C(=O)OH} as an acidic group because of their higher adhesive strength to a tooth.

Component (A) in a dental adhesive composition of this invention may be composed of the acidic-group containing polymerizable monomer alone. It is, however, preferable that the composition further contain a polymerizable monomer without an acidic group because a cured product of the adhesive composition mixture exhibits good strength and adhesion durability. In particular, a content of the acidic-group containing polymerizable monomer in the total of polymerizable monomers as component (A) is preferably 3 to 70 wt %, more preferably 5 to 50 wt % because it can improve an adhesive strength to both dental enamel and dentin. If a content of the acidic-group containing polymerizable monomer is too small, an adhesive strength to a dental enamel tends to be reduced, while if it is too large, an adhesive strength to a dentin tends to be reduced.

A polymerizable monomer without an acidic group may be any known monomer having at least one polymerizable unsaturated group in a molecule other than the above acidic-group containing polymerizable monomers, without limitations. A polymerizable unsaturated group in the polymerizable monomer may be selected from those described for the acidic-group containing polymerizable monomer, and preferable examples include acryloyl group, methacryloyl group, acrylamide group and methacrylamide group because of their appropriate curing rate.

Preferable examples of a polymerizable monomer other than acidic-group containing polymerizable monomers include mono(meth)acrylate monomers such as methyl (meth)acrylate, ethyl (meth)acrylate, butyl (meth)acrylate, glycidyl (meth)acrylate, 2-cyanomethyl (meth)acrylate, benzyl (meth)acrylate, polyethylene glycol mono(meth) acrylate, allyl (meth)acrylate, 2-hydroxyethyl (meth) acrylate, 3-hydroxypropyl (meth)acrylate and glyceryl mono(meth)acrylate; polyfunctional (meth)acrylate monomers such as ethylene glycol di(meth)acrylate, diethyleneglycol di(meth)acrylate, triethyleneglycol di(meth)acrylate, nonaethyleneglycol di(meth)acrylate, propyleneglycol di(meth)acrylate, dipropyleneglycol di(meth)acrylate, 2,2'-bis[4-(meth)acryloyloxyethoxyphenyl]propane, 2,2'-bis[4-(meth)acryloyloxyethoxyethoxyphenyl]propane, 2,2'-bis[4-(meth)acryloyloxyethoxyethoxyethoxyethoxyethoxyphenyl]propane, 2,2'-bis{4-[3-(meth)acryloyloxy-2-hydroxypropoxy]phenyl}propane, 1,4-butanediol di(meth)acrylate, 1,6-hexanediol di(meth)acrylate, 1,9-nonandiol di(meth)acrylate, trimethylolpropane tri(meth)acrylate, neopentylglycol di(meth)acrylate, 1,6-bis(methacrylethyloxycarbonylamino)-2,2,4-trimethylhexane, 1,6-bis(methacrylethyloxycarbonylamino)-2,4,4-trimethylhexane, urethane (meth)acrylate and epoxy (meth)acrylate; fumarate monomers such as monomethyl fumarate, diethyl fumarate and diphenyl fumarate; styrene or α-methyl styrene derivatives such as styrene, divinylbenzene, α-methyl styrene and α-methyl styrene dimer; and allyl compounds such as diallyl phthalate, diallyl terephthalate, diallyl carbonate and allyl diglycolcarbonate.

When cementing a noble-metal restorative material for a tooth crown with a tooth, it is preferable to add a polymerizable monomer containing a functional group capable of binding to the noble metal as a polymerizable monomer without an acidic group in component (A). Examples of such a polymerizable monomer include functional-group containing monomers such as derivative of thiouracils, triazine dithiones and mercaptothiazoles. Specific examples include polymerizable monomers which can generate a mercapto group by tautomerism, represented by general formulas (3) to (7); polymerizable monomers containing a disulfide groups represented by general formulas (8) to (11); and polymerizable monomers containing a linear or cyclic thioether group represented by general formulas (12) and (13):

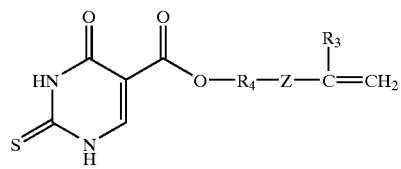

(3)

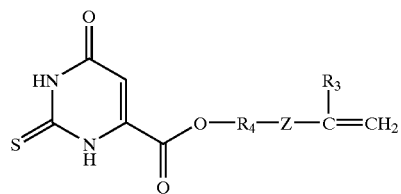

(4)

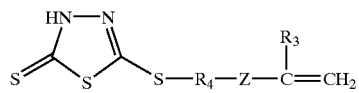

(5)

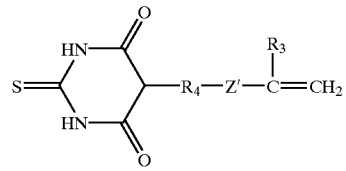

(6)

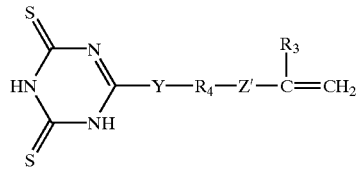

(7)

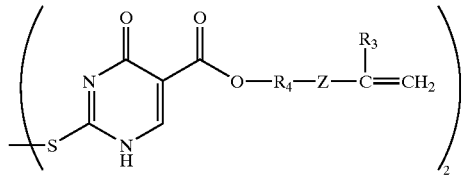

(8)

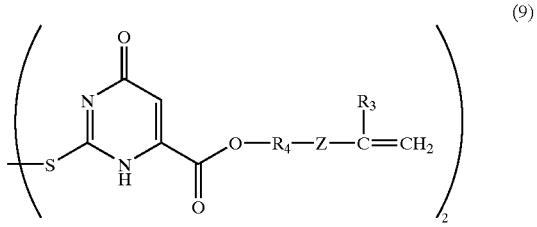

(9)

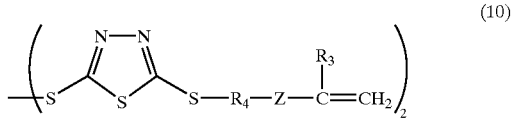

(10)

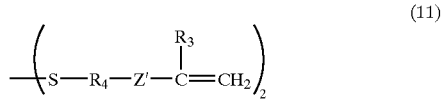

(11)

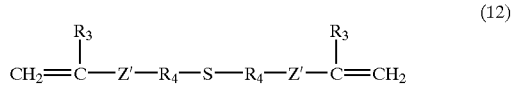

(12)

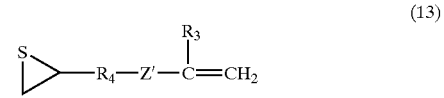

(13)

wherein $R_3$ represents hydrogen atom or methyl group; $R_4$ represents a bivalent $C_1$ to $C_{12}$ saturated hydrocarbon group, $-CH_2-C_6H_4-CH_2-$, $-(CH_2)_o-Si(CH_3)_2OSi(CH_3)_2-(CH_2)_p-$ where o and p independently represent an integer of 1 to 5, or $-CH_2CH_2OCH_2CH_2-$; Z represents $-OCO-$, $-OCH_2-$ or $-OCH_2-C_6H_4-$ in any of which the carbon atom at the right end is bound to an unsaturated carbon atom while the oxygen atom at the left end is bound to $R_4$; Z' is $-OCO-$, $-C_6H_4-$ or a single bond, provided that when it is $-OCO-$, the carbon atom at the right end is bound to an unsaturated carbon atom while the oxygen atom at the left end is bound to $R_4$; Y is $-S-$, $-O-$ or $-N(R')-$ where R' is hydrogen atom or $C_1$ to $C_5$ alkyl group. An expression "Z' is a single bond" herein means that $R_4$ and an unsaturated carbon is bound directly.

Among specific examples of such a compound, examples of a polymerizable monomer which can generate a mercapto group by tautomerism, represented by general formulas (3) to (7) are as follows.

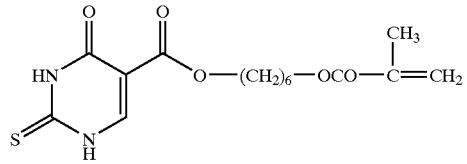

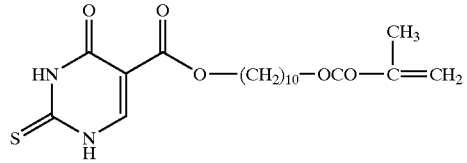

-continued

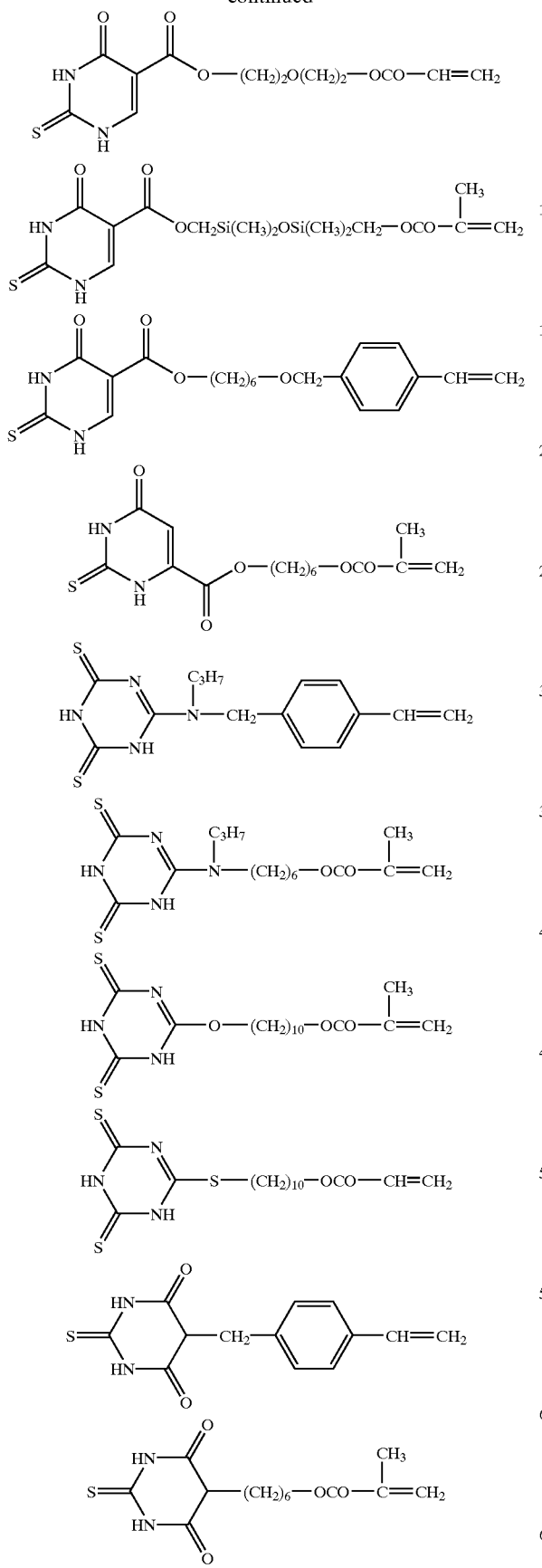

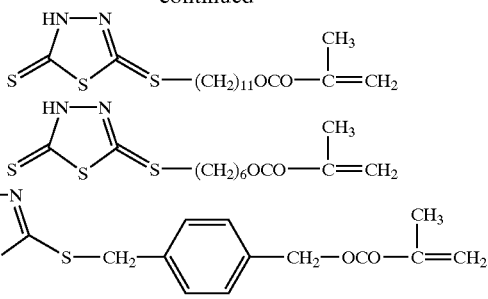

Examples of a polymerizable monomer having a disulfide group represented by general formulas (8) to (11) are as follows.

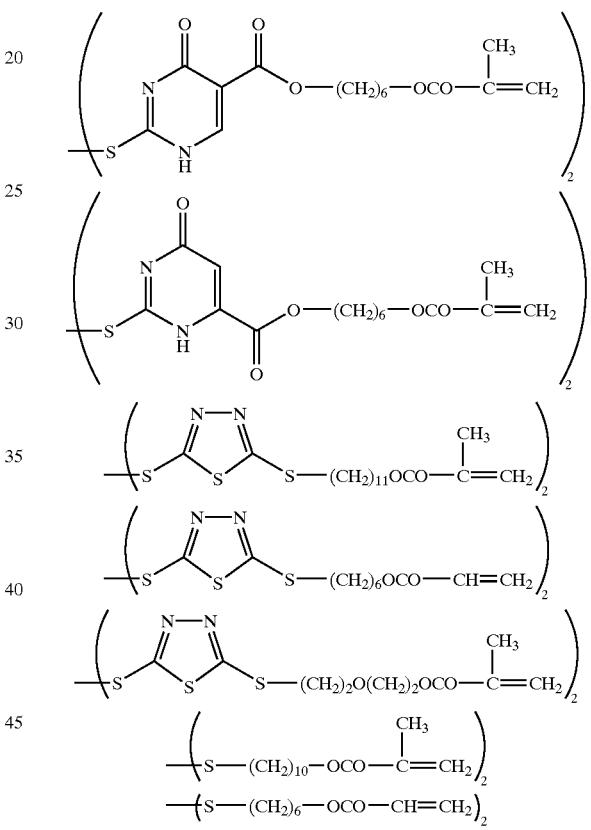

Examples of a polymerizable monomer having a linear or cyclic thioether group represented by general formulas (12) and (13) are as follows.

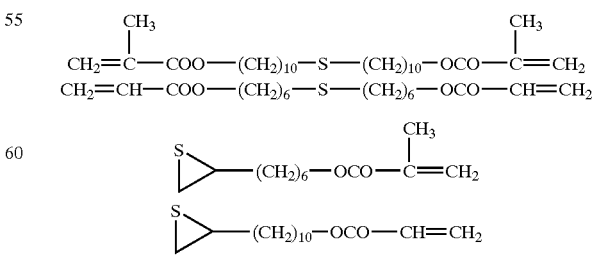

These polymerizable monomers having a functional group capable of being bound to a noble metal may be used alone or in combination of two or more. A content of these polymerizable monomers can be appropriately determined, taking a viscosity of a composition and mechanical strength of a cured product of an adhesive composition into consideration, and is generally 0.1 to 50 wt parts, more preferably 0.2 to 20 wt parts to 100 wt parts of the total amount of polymerizable monomers.

There are no restrictions to a content of a polymerizable monomer comprising an acidic-group containing polymerizable monomer as component (A) in an adhesive composition of this invention. It is, however, preferably 25 to 65 wt parts, more preferably 30 to 60 wt parts, particularly preferably 35 to 55 wt parts to 100 wt parts of the total amount of a polymerizable monomer comprising an acidic-group containing polymerizable monomer as component (A), a non-crosslinking polymer filler as component (B) and a polymerization initiator as component (C), in order to maintain solubility of the non-crosslinking polymer filler and a working time within preferable ranges.

(B) A Spherical Filler Substantially Consisting of Non-crosslinking Polymethyl Methacrylate and a Spherical Filler Substantially Consisting of Non-crosslinking Polyethyl Methacrylate Component (B) in an adhesive composition of this invention comprises as essential ingredients a spherical filler substantially consisting of non-crosslinking polymethyl methacrylate (hereinafter, referred to as a "PMMA spherical filler") and a spherical filler substantially consisting of non-crosslinking polyethyl methacrylate (hereinafter, referred to as a "PEMA spherical filler"). If component (B) is not a mixture of these two fillers, an appropriate working time cannot be achieved.

For example, if component (B) consists of the PMMA spherical filler alone, a dissolution rate to a polymerizable monomer of component (A) is significantly reduced and the filler is not so compatible with the monomer, so that it takes a longer time to dissolve the filler until it has properties suitable to handling. If only the PEMA spherical filler is employed, a working time is extremely reduced.

There are no restrictions to the PMMA and the PEMA spherical fillers used as component (B) as long as they are substantially non-crosslinking. Examples of these fillers are spherical polymers prepared by suspension polymerization or emulsion polymerization of methyl methacrylate or ethyl methacrylate without using a crosslinking agent. Such spherical fillers are commercially and industrially available. The term "substantially non-crosslinking" as used herein means that most of a polymer is dissolved in a monomer component as component (A). If a crosslinking density is too high for the filler polymer to be dissolved in the monomer, mixing of these components cannot give good handling properties due to poor compatibility and also cannot give a good adhesive strength. The term "spherical" as used herein means that a filler has a generally round shape without an acute-angle part as is found in a pulverized filler, and thus does not necessarily means an entirely spheric shape.

The PMMA and PEMA spheric fillers must not be necessarily homopolymers of methyl methacrylate and ethyl methacrylate, respectively. They may be copolymers with a different monomer as long as the other monomer is contained within a range that it does not adversely affect the effects desired in this invention (generally, 10 mol % or less based on the monomer amount). Examples of the different monomer include alkyl (meth)acrylates such as methyl (meth)acrylate, ethyl (meth)acrylate, propyl (meth)acrylate, butyl (meth)acrylate, 2-hydroxyethyl (meth)acrylate, 2-hydroxypropyl (meth)acrylate and 3-hydroxypropyl (meth)acrylate; and styrene monomers such as styrene, α-methylstyrene and para-methylstyrene.

There are no restrictions to a weight average molecular weight of each polymer in a PMMA or PEMA spherical filler used. However, the PMMA spherical filler is suitably a mixture of a spherical filler consisting of a non-crosslinking polymethyl methacrylate having a weight average molecular weight of less than 100,000 (hereinafter, referred to as a low-molecular weight PMMA spherical filler) and a spherical filler consisting of a non-crosslinking polymethyl methacrylate having a weight average molecular weight of 100,000 or more (hereinafter, referred to as a high-molecular weight PMMA spherical filler), improving compatibility of the fillers and monomers when the dental adhesive composition mixture of the present invention is cured. A mixing ratio between the spherical filler consisting of a non-crosslinking polymethyl methacrylate having a weight average molecular weight of less than 100,000 and the spherical filler consisting of a non-crosslinking polymethyl methacrylate having a weight average molecular weight of 100,000 or more is preferably 10:90 to 70:30 by weight.

There are no restrictions to a weight average molecular weight of the non-crosslinking polyethyl methacrylate constituting the PEMA spherical filler because it does not significantly influence a working time, and commonly available fillers generally have a weight average molecular weight of about 100,000 to 500,000. Herein, a weight average molecular weight is a molecular weight converted into polystyrene as determined by gel permeation chromatography.

There are no restrictions to a particle size of a PMMA or PEMA spherical filler. It, however, preferably has an average particle size of 0.1 to 50 $\mu$m, particularly preferably 1 to 40 $\mu$m in the light of reduction in a film thickness and a higher adhesive strength of an adhesive composition.

A mixing ratio between a PMMA and a PEMA spherical fillers influences a working time. An optimal ratio cannot be particularly defined because it is dependent on a particle size of a filler used and a molecular weight of a polymer constituting the filler. A proportion of the amount of the PMMA spherical filler to the total amount of non-crosslinking polymer fillers is generally 85 to 98 wt %. Within this range, a suitable range may be appropriately determined, taking a working time and a curing time in each system into consideration. A mixing ratio can be determined such that a working time of an adhesive composition determined at room temperature (23° C.) is 40 to 150 sec, preferably 60 to 120 sec and a curing time determined at 37° C. is 3 to 5 min. Generally, a larger ratio of the PMMA spherical filler tends to increase a working time and thus a curing time.

A working time as used above is defined a time period from a start time when after adding component (B) to component (A) at a room temperature (23° C.) the mixture has an appropriate viscosity, i. e., the mixture becomes viscous such that it can be taken with the spatula, by stirring the mixture with a stirring spatula for a few (2 to 3) seconds with an interval of 5 sec to an endpoint when a viscosity of the mixture is increased such that the mixture can be taken as a thread with the spatula (i. e., a period during which a viscosity is proper for handling).

If it takes a longer time to increase a viscosity of the mixture to the above proper level (a proper-viscosity reaching time) by stirring, the adhesive composition remains to be a low-viscosity liquid for a long time. Since the composition cannot be applied to a tooth during the period, a dentist must continue stirring until a proper viscosity is provided, which is a clinically troublesome procedure. A mixing ratio of these two fillers is, therefore, preferably determined such that a proper-viscosity reaching time becomes 10 to 40 sec, particularly 20 to 35 sec.

A curing time is determined as follows. After blending components (A), (B) and (C), the mixture is stirred as described above. A sample mixture whose viscosity has reached a proper level is observed for its rest curing behavior at 37° C. using a differential scanning calorimeter (DSC) to determine a time until the maximum curing heat is observed. A curing time is a period from mixing to the time of the maximum curing heat in the above procedure.

There are no restrictions to a content of component (B) in an adhesive composition of this invention. It is, however, preferably 35 to 70 wt parts, more preferably 40 to 65 wt parts, particularly 45 to 60 wt parts to 100 wt parts of the total of components (A), (B) and (C).

(c) Polymerization Initiator

There are no restrictions to a polymerization initiator as component (C) used in an adhesive composition of this invention, and any chemical-polymerization initiator or photopolymerization initiator used in a conventional dental curable composition can be used without limitations. Tributylboran or its partially oxidized as a polymerization initiator has disadvantages that it must be enclosed in a special syringe while being separated from other components and it reduces a curing rate, but they can be used.

Chemical-polymerization initiators which can be used in this invention include redox type initiators such as an organic peroxide/an amine and an organic peroxide/an amine/a sulfinic acid salt; an organometallic initiator which initiate polymerization by reacting with an acid; and a (thio)balbituric acid derivative/cupric ion/a halogenated compound.

Preferable examples of the above organic peroxide include t-butyl hydroperoxide, cumene hydroperoxide, di-t-butyl peroxide, dicumyl peroxide, acetyl peroxide, lauroyl peroxide and benzoyl peroxide. Examples of the amine preferably include secondary and tertiary amines, in which an amino group is attached to an aryl group such as N,N-dimethyl-p-toluidine, N,N-dimethylaniline, N-(2-hydroxyethyl)aniline, N,N-di(2-hydroxyethyl)-p-toluidine, N-methylaniline and N-methyl-p-toluidine. Examples of the above sulfinic acid salt which can be suitably used include sodium benzenesulfinate, lithium benzenesulfinate, sodium p-toluenesulfinate, lithium p-toluenesulfinate, potassium p-toluenesulfinate, sodium m-nitrobenzenesulfinate and sodium p-fluorobenzenesulfinate.

An organometallic polymerization initiator which can initiate polymerization by reacting with an acid is suitably an aryl borate represented by general formula (14) described later. Preferable examples of the above (thio)balbituric acid derivative include 5-butyl (thio)balbituric acid, 1,3,5-trimethyl (thio)balbituric acid, 1-benzyl-5-phenyl (thio) balbituric acid, 1-cyclohexyl-5-methyl (thio)balbituric acid and 1-cyclohexyl-5-butyl (thio)balbituric acid. Preferable examples of the above halogenated compound include dilauryl-dimethyl-ammonium chloride, lauryl-dimethylbenzyl-ammonium chloride, benzyl-trimethylammonium chloride, tetramethyl-ammonium chloride, benzyl-dimethyl-cetyl-ammonium chloride and dilauryl-dimethyl-ammonium bromide.

A photopolymerization initiator which can be used in this invention may consist of a photosensitizer alone; a photosensitizer/a photopolymerization promoter; a dye/a photoacid generator/a sulfinic acid salt; or a dye/a photoacid generator/an aryl borate.

Examples of a photosensitizer include $\alpha$-diketones such as camphorquinone, benzil, $\alpha$-naphthyl, acenaphthene, naphthoquinone, p,p'-dimethoxybenzil, p,p'-dichlorobenzylacetyl, 1,2-phenanthrenequinone, 1,4-phenanthrenequinone, 3,4-phenanthrenequinone and 9,10-phenanthrenequinone; thioxanthones such as 2,4-diethylthioxanthone; $\alpha$-aminoacetophenones such as 2-benzyl-dimethylamino-1-(4-morpholinophenyl)-butanone-1,2-benzyl-diethylamino-1-(4-morpholinophenyl)-butanone-1,2-benzyl-dimethylamino-1-(4-morpholinophenyl)-propanone-1,2-benzyl-diethylamino-1-(4-morpholinophenyl)-propanone-1,2-benzyl-dimethylamino-1-(4-morpholinophenyl)-pentanone-1 and 2-benzyl-diethylamino-1-(4-morpholinophenyl)-pentanone-1; and acylphosphine oxides such as 2,4,6-trimethylbenzoyldiphenylphosphine oxide, bis(2,4,6-trimethylbenzoyl)phenylphosphine oxide and bis(2,6-dimethoxybenzoyl)-2,4,4-trimethylpentylphosphine oxide.

Preferable examples of a photopolymerization promoter include tertiary amines such as N,N-dimethylaniline, N,N-diethylaniline, N,N-di-n-butylaniline, N,N-dibenzylaniline, N,N-dimethyl-p-toluidine, N,N-diethyl-p-toluidine, N,N-dimethyl-m-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, ethyl p-dimethylaminobenzoate, amyl p-dimethylaminobenzoate, methyl N,N-dimethylanthranate, N,N-dihydroxyethylaniline, N,N-dihydroxyethyl-p-toluidine, p-dimethylaminophenetyl alcohol, p-dimethylaminostilbene, N,N-dimethyl-3,5-xylidine, 4-dimethylaminopyridine, N,N-dimethyl-$\alpha$-naphthylamine, N,N-dimethyl-$\beta$-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino)diethanol; and balbituric acids such as 5-butylbalbituric acid and 1-benzyl-5-phenylbalbituric acid.

Preferable examples of a dye include 3-thienoylcoumarin, 3-(4-methoxybenzoyl)coumarin, 3-benzoylcoumarin, 3-(4-cyanobenzoyl)coumarin, 3-thienoyl-7-methoxycoumarin, 7-methoxy-3-(4-methoxybenzoyl)coumarin, 3-benzoyl-7-methoxycoumarin, 3-(4-cyanobenzoyl)-7-methoxycoumarin, 5,7-dimethoxy-3-(4-methoxybenzoyl) coumarin, 3-benzoyl-5,7-dimethoxycoumarin, 3-(4-cyanobenzoyl)-5,7-dimethoxycoumarin, 3-acetyl-7-dimethylaminocoumarin, 7-diethylamino-3-thienoylcoumarin, 7-diethylamino-3-(4-methoxybenzoyl) coumarin, 3-benzoyl-7-diethylaminocoumarin, 7-diethylamino-3-(4-cyanobenzoyl)coumarin, 7-diethylamino-3-(4-dimethylaminobenzoyl)coumarin, 3-cinnamoyl-7-diethylaminocoumarin, 3-(p-diethylaminocinnamoyl)-7-diethylaminocoumarin, 3-acetyl-7-diethylaminocoumarin, 3-carboxy-7-diethylaminocoumarin, 3-(4-carboxybenzoyl)-7-diethylaminocoumarin, 3,3'-carbonylbiscoumarin, 3,3'-carbonylbis(7-diethylamino)coumarin, 2,3,6,7-tetrahydro-1,1,7,7-tetramethyl-10-(benzothiazolyl)-11-oxo-1H,5H, 11H-[1]benzopyrano[6,7,8,ij]quinolizine, 3,3'-carbonylbis(5,7-)dimethoxy-3,3'-biscoumarin, 3-(2'-benzimidazolyl)-7-diethylaminocoumarin, 3-(2'-benzoxazolyl)-7-diethylaminocoumarin, 3-(5'-phenylthiadiazolyl)-7-diethylaminocoumarin, 3-(2'-benzthiazolyl)-7-diethylaminocoumarin and 3,3'-carbonylbis(4-cyano-7-diethylamino)coumarin.

Examples of a photoacid generator which can be used include halomethyl-substituted-s-triazines such as 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-(p-methoxyphenyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-(p-methoxystyryl)-4,6-bis(trichloromethyl)-s-triazine, 2-(o-methoxystyryl)-4,6-bis(trichloromethyl)-s-triazine, 2-(p-butoxystyryl)-4,6-bis(trichloromethyl)-s-triazine, 2-(3,4-dimethoxystyryl)-4,6-bis(trichloromethyl)-s-triazine and 2-(3,4,5-trimethoxystyryl)-4,6-bis(trichloromethyl)-s-triazine; and diphenyliodonium salts such as diphenyliodonium, bis(p-chlorophenyl)iodonium, ditolyliodonium, bis(p-tert-butylphenyl)iodonium, bis(m-nitrophenyl)iodonium, p-tert-butylphenylphenyliodonium, methoxyphenylphenyliodonium and p-octyloxyphenylphenyliodonium chlorides, bromides, tetrafluoroborates, hexafluorophosphates, hexafluoroarsenates, hexafluoroantimonates and trifluoromethanesulfonates.

As a sulfinic acid salt, those specifically listed for the redox type polymerization initiator can be also used and as an arylborate compound, those represented by general formula (14) described later can be used.

These polymerization initiators can be, as appropriate, added alone or in combination of two or more.

In a dental adhesive composition of this invention, a chemical polymerization initiator consisting of a combination of a peroxide such as benzoyl peroxide and an amine such as dimethyl-p-toluidine can be suitably used as component (C), a polymerization initiator, because it can provide an improved adhesive strength and allows a polymerization rate (curing rate) to be properly adjusted. When a dental adhesive composition of this invention is of a dual curing type, it is suitable in the light of an adhesive strength and improvement in polymerizability to use the above chemical polymerization initiator in combination with a photopolymerization initiator consisting of a combination of an α-diketone such as camphorquinone and an amine such as ethyl dimethylaminobenzoate or of an acylphosphine oxide derivative such as bis(2,4,6-trimethylbenzoyl)phenylphosphine oxide.

The content of a polymerization initiator as component (C) in a dental adhesive composition of this invention is not particularly limited as long as it is sufficient to initiate polymerization of monomer components, and it is preferably 0.01 to 20 wt parts to 100 wt parts of the total amount of polymerizable monomers as component (A) in the light of improvement in physical properties such as weather resistance of a cured product.

In addition to component (B), a dental adhesive composition of this invention can contain an inorganic filler for adjusting physical properties such as cured-product strength for the composition. The inorganic filler may be selected from common inorganic fillers without limitations.

Examples of an inorganic filler which can be used in this invention include quartz, silica, silica-alumina, silica-titania, silica-zirconia, silica-magnesia, silica-calcia, silica-barium oxide, silica-strontium oxide, silica-titania-sodium oxide, silica-titania-potassium oxide, silica-zirconia-sodium oxide, silica-zirconia-potassium oxide, titania, zirconia and alumina.

An ion-releasing filler which can release cations in an acidic solution may be also suitably used. Examples of such an ion-releasing filler include hydroxides such as calcium hydroxide and strontium hydroxide; zinc oxide; silicate glass; fluoroaluminosilicate glass; barium glass; and strontium glass. Among these, fluoroaluminosilicate glass is most preferable in that its cured product exhibits good stain resistance. The fluoroaluminosilicate glass may be selected from those known for a dental cement. A commonly used fluoroaluminosilicate glass has the following composition: 10 to 33% of silicon; 4 to 30% of aluminum; 5 to 36 of alkaline earth metals; 0 to 10% of alkali metals; 0.2 to 16% of phosphorous; 2 to 40% of fluorine; and the remaining amount of oxygen in an ion-weight percent. Suitable are those having the above composition, those in which a part or all of the alkaline earth metal component is replaced with magnesium, strontium and/or barium, and those containing strontium for providing a cured product with X-ray opacity and improved strength.

These inorganic fillers may be preferably coated with a methacrylate polymer such as polymethyl methacrylate and polyethyl methacrylate for improving compatibility with the above polymerizable monomers. An inorganic-organic composite filler such as ground complex of inorganic oxide and polymer may be also used.

There are no restrictions to a shape of such a filler, and thus it may be presented as pulverized particles prepared by common grinding or spherical particles. There are no restrictions to a particle size of the filler and it is preferably 50 $\mu$m or less, more preferably 30 $\mu$m or less for providing a film thickness required for good adhesion of a prosthesis to a tooth.

In a dental adhesive composition of this invention, an organic solvent, a thickener or the like may be added for adjusting a viscosity of the composition as long as the additive does not deteriorate performance of the composition. An organic solvent is desirably selected from those which are not harmful to a living body, preferably including ethanol, propanol, ethyleneglycol, propane diol and acetone. Such an organic solvent may be, if necessary, a mixture of two or more organic solvents. Furthermore, a small amount of a polymerization inhibitor may be preferably added for improving storage stability and environmental light stability, including hydroquinone, hydroquinone monomethyl ether and 2,6-di-tert-butylphenol. If necessary, an appropriate amount of a colorant may be added to a dental adhesive composition of this invention. Their contents may be determined as usual.

In a dental adhesive composition of this invention, mixing of component (B) and component (A) results in increase in a viscosity of the mixture because of dissolution of component (B). It is, therefore, preferable to separately prepare these components for preventing them from being mixed each other and then to mix them immediately before use. Generally, component (A) and component (B) are separately packed. A polymerization initiator as component (C) can be packed as a premix with component (A) or (B) in a condition of preventing initiation of polymerization.

Primer

When using a dental adhesive of this invention for, e. g., restoring a tooth, the tooth usually undergoes primer treatment that an infiltration promoter known as a primer is applied on the surface of the tooth before applying the composition. This primer treatment is conducted for improving adhesiveness. The primer may be any of known dental primers.

A dental adhesive composition of this invention may be used in combination with a dental primer comprising (D) an acidic-group containing polymerizable monomer, (E) an aryl borate, (F) an organosulfinic acid salt and (G) water, to provide further improved adhesion performance.

A dental adhesive composition of this invention may be used in combination with a dental primer comprising (D) an acidic-group containing polymerizable monomer, (E) an aryl borate, (F) an organosulfinic acid salt, (G) water, (H) a polymerizable monomer other than the acidic-group containing polymerizable monomer and (I) an organic solvent, to provide further improved adhesion performance.

A dental adhesive composition of this invention may be used in combination with the primer composition as a kit (the present kit), to achieve both good operability and improved adhesive strength.

(D) Acidic-group Containing Polymerizable Monomer

Component (D) in a primer composition used in the present kit is an acidic-group containing polymerizable monomer. The acidic-group containing polymerizable monomer is as described for the acidic-group containing polymerizable monomer in component (A) described above. The acidic-group containing polymerizable monomer used as component (D) must not be necessarily the same as that in combination therewith as component (A) in the dental adhesive composition of this invention. Monomers used as component (D) may be used alone or in combination of two or more, as appropriate. A content of component (D) is 1 to 50 wt parts, preferably 2 to 30 wt parts, more preferably 3 to 25 wt parts to 100 wt parts of the total of the primer components in the light of improvement in adhesiveness to a dental enamel and a dentin.

(E) Aryl Borate

An aryl borate used as component (E) in the above primer composition is a borate having at least one boron-aryl bond in one molecule. A borate without an intramolecular boron-aryl bond exhibit inadequate storage stability. An aryl borate suitably used in this invention may be represented by general formula (14):

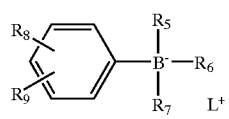

(14)

wherein $R_5$, $R_6$ and $R_7$ are independently optionally substituted alkyl group, aryl group, aralkyl group or alkenyl group; R8 and R9 are independently hydrogen atom, halogen atom, nitro group, optionally substituted alkyl group, optionally substituted alkoxyl group or optionally substituted phenyl group; $L^+$ is a metal cation, a quaternary ammonium ion, a quaternary pyridinium ion, a quaternary quinolinium ion or a phosphonium ion.

Among the above aryl borates, aryl borates which can be suitably used will be specifically described.

Examples of a borate having one aryl group include sodium salts, lithium salts, potassium salts, magnesium salts, tetrabutylammonium salts, tetramethylammonium salts, tetraethylammonium salts, triethanolamine salts, methylpyridinium salts, ethylpyridinium salts, butylpyridinium salts, methylquinolium salts, ethylquinolium salts and butylquinolinium salts of trialkylphenylborons, trialkyl(p-chlorophenyl)borons, trialkyl(p-fluorophenyl)borons, trialkyl(3,5-bistrifluoromethyl)phenylborons, trialkyl[3,5-bis(1,1,1,3,3,3-hexafluoro-2-methoxy-2-propyl)phenyl]borons, trialkyl(p-nitrophenyl)borons, trialkyl(m-nitrophenyl)borons, trialkyl(p-butylphenyl)borons, trialkyl(m-butylphenyl)borons, trialkyl(p-butyloxyphenyl)borons, trialkyl(m-butyloxyphenyl)borons, trialkyl(p-octyloxyphenyl)borons and trialkyl(m-octyloxyphenyl)borons, where the alkyl group includes n-butyl group, n-octyl group and n-dodecyl group and the like.

Examples of a borate having two aryl groups include sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolium salts, ethylquinolium salts and butylquinolinium salts of dialkyl-diphenylborons, dialkyl-di(p-chlorophenyl)borons, dialkyl-di(p-fluorophenyl)borons, dialkyl-di(3,5-bistrifluoromethyl)phenylborons, dialkyl-di[3,5-bis(1,1,1,3,3,3-hexafluoro-2-methoxy-2-propyl)phenyl]borons, dialkyl-di(p-nitrophenyl)borons, dialkyl-di(m-nitrophenyl)borons, dialkyl-di(p-butylphenyl)borons, dialkyl-di(m-butylphenyl)borons, dialkyl-di(p-butyloxyphenyl)borons, dialkyl-di(m-butyloxyphenyl)borons, dialkyl-di(p-octyloxyphenyl)borons and dialkyl-di(m-octyloxyphenyl)borons, where the alkyl group is as described above.

Examples of a borate having three aryl groups include sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolium salts, ethylquinolium salts and butylquinolinium salts of monoalkyl-triphenylborons, monoalkyl-tri(p-chlorophenyl)borons, monoalkyl-tri(p-fluorophenyl)borons, monoalkyl-tri(3,5-bistrifluoromethyl)phenylborons, monoalkyl-tri[3,5-bis(1,1,1,3,3,3-hexafluoro-2-methoxy-2-propyl)phenyl]borons, monoalkyl-tri(p-nitrophenyl)borons, monoalkyl-tri(m-nitrophenyl)borons, monoalkyl-tri(p-butylphenyl)borons, monoalkyl-tri(m-butylphenyl)borons, monoalkyl-tri(p-butyloxyphenyl)borons, monoalkyl-tri(m-butyloxyphenyl)borons, mono alkyl-tri(p-octyloxyphenyl)borons and monoalkyl-tri(m-octyloxyphenyl)borons, where the alkyl group include n-butyl group, n-octyl group and n-dodecyl group and the like.

Examples of a borate having four aryl groups include sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolium salts, ethylquinolium salts and butylquinolinium salts of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron and tetrakis(m-octyloxyphenyl)boron.

Among these, a borate having three or four aryl groups may be suitably used for further improving storage stability. Furthermore, a borate having four aryl groups is most preferable because of its good handling properties and availability. The aryl borates may be used alone or in combination of two or more.

The aryl borate is preferably used at 0.01 to 25 wt parts to 100 wt parts of the total of the polymerizable monomers in the primer composition, i. e., the total of an acidic-group containing polymerizable monomer as component (D) and other polymerizable monomers added as optional components. Its content is more preferably 0.05 to 15 wt parts in the light of good polymerization properties in an adhesive interface and a higher adhesive strength.

(F) Organosulfinic Acid Salt

An organosulfinic acid salt as component (F) in a dental primer in the present kit may be selected from alkali metal, alkaline earth metal and ammonium salts of known organosulfinic acids. Examples of the alkali metal salt include lithium, sodium and potassium salts. Examples of the alkaline earth metal salt include magnesium, calcium, strontium and barium salts. Examples of the amine salt include primary ammonium salts such as methylamine, ethylamine, propylamine, butylamine, aniline, toluidine, phenylenediamine and xylylenediamine salts; secondary ammonium salts such as dimethylamine, diethylamine, dipropylamine, dibutylamine, piperidine, N-methylaniline, N-ethylaniline, diphenylamine and N-methyltoluidine; tertiary ammonium salts such as trimethylamine, triethylamine, pyridine, N,N-di(β-hydroxyethyl)aniline, N,N-diethylaniline, N,N-dimethyltoluidine and N,N-di(β-hydroxyethyl)toluidine salts; and quaternary ammonium salts such as tetramethylammonium, tetraethylammonium, tetrapropylammonium, and trimethylbenzylammonium salts.

A suitable organosulfinic acid which may form a salt with these metals and amines may be a known sulfinic acid such as alkylsulfinic acids, alicyclic sulfinic acids and aromatic sulfinic acids.

Examples of an organosulfinic acid salt include alkylsulfinic acid salts such as sodium ethanesulfinate, lithium ethanesulfinate, sodium propanesulfinate, calcium hexanesulfinate, sodium octanesulfinate, sodium decanesulfinate and sodium dodecanesulfinate; alicyclic sulfinic acid salts such as sodium cyclohexanesulfinate and sodium cyclooctanesulfinate; and aromatic sulfinic acid salts such as lithium benzenesulfinate, sodium benzenesulfinate, potassium benzenesulfinate, magnesium benzenesulfinate, calcium benzenesulfinate, strontium benzenesulfinate, barium benzenesulfinate, butylamine benzenesulfinate, aniline benzenesulfinate, toluidine benzenesulfinate, phenylenediamine benzenesulfinate, diethylamine benzenesulfinate, diphenylamine benzenesulfinate, triethylamine benzenesulfinate, ammonium benzenesulfinate, tetramethylammonium benzenesulfinate, trimethylbenzylammonium benzenesulfinate, lithium o-toluenesulfinate, sodium o-toluenesulfinate, calcium o-toluenesulfinate, cyclohexylamine o-toluenesulfinate, aniline o-toluenesulfinate, ammonium o-toluenesulfinate, tetraethylammonium o-toluenesulfinate, lithium p-toluenesulfinate, sodium p-toluenesulfinate, potassium p-toluenesulfinate, barium p-toluenesulfinate, ethylamine p-toluenesulfinate, toluidine p-toluenesulfinate, N-methylaniline p-toluenesulfinate, pyridinium p-toluenesulfinate, ammonium p-toluenesulfinate, tetrabutylammonium p-toluenesulfinate, sodium β-naphthalenesulfinate, strontium β-naphthalenesulfinate, triethylamine β-naphthalenesulfinate, N-methyltoluidine β-naphthalenesulfinate, ammonium β-naphthalenesulfinate and trimethylbenzylammonium β-naphthalenesulfinate.

Among these sulfinic acid salts, sodium and lithium salts of aromatic sulfinates are preferable because of their catalytic activity to a tooth and availability. These organic sulfinic acid salts may be used alone or in combination of two or more.

An organic sulfinic acid salt is preferably added at 0.01 to 25 wt parts to 100 parts of the total amount of polymerizable monomers in the primer composition, more preferably at 0.05 to 15 wt parts in the light of higher polymerizability in an adhesion interface and an improved adhesive strength.

(G) Water

Preferably, component (G), water, in the primer composition in the present kit is substantially free from impurities which are detrimental to storage stability, biocompatibility or adhesiveness. The types of water which can be used include deionized water and distilled water. Water is contained at 5 to 95 wt parts, preferably 20 to 80 wt parts, more preferably 30 to 75 wt parts to 100 parts of the total of components in the primer for improving an adhesive strength to both dental dentin and enamel.

(H) Polymerizable Monomer other than the Acidic-group Containing Polymerizable Monomer A dental primer composition used in the present kit preferably comprises a polymerizable monomer other than the acidic-group containing polymerizable monomer as component (H) for adjusting a viscosity, improving strength or adjusting other physical properties in the primer composition. A polymerizable monomer as component (H) may be selected from those listed for a polymerizable monomer other than an acidic-group containing polymerizable monomer in component (A) in a dental adhesive composition of this invention. This polymerizable monomer must not be necessarily the same as that used as component (A) in the dental adhesive composition of this invention. Such monomers may be used alone or in combination of two or more, as appropriate.

A content of component (H) is preferably 5 to 100 wt parts, more preferably 10 to 75 wt parts to 100 wt parts of component (D).

(I) Organic Solvent

A dental primer used in the present kit preferably comprises an organic solvent as component (I). The organic solvent is added for dissolving, if used, non-aqueous polymerizable monomers to give a homogeneous solution.

Examples of an organic solvent include water-miscible organic solvents including alcohols and ethers such as methanol, ethanol, 1-propanol, 2-propanol, isopropanol, 1-butanol, 2-butanol, 2-methyl-1-propanol, 2-methyl-2-propanol, 2-methyl-2-butanol, 2-propen-1-ol, 2-propyn-1-ol, 1,2-ethanediol, 1,2-propanediol, 1,3-propanediol, 1,3-butanediol, 1,4-butanediol, 2,3-butanediol, 1,5-pentanediol, hexyleneglycol, glycerol, 1,2,6-hexanetriol, trimethylolpropane, diethyleneglycol, triethyleneglycol, tetraethyleneglycol, propyleneglycol, dipropyleneglycol, tripropyleneglycol, 2-methoxyethanol, 2-ethoxyethanol, 2-(methoxyethoxy)ethanol, 2-(ethoxyethoxy)ethanol, triethyleneglycol monomethyl ether, triethyleneglycol monoethyl ether, 2-isopropoxyethanol, 2-butoxyethanol, 1-methoxy-2-propanol, 1-ethoxy-2-propanol, dipropyleneglycol monomethyl ether, tripropyleneglycol monomethyl ether, 1,3-dioxolane, tetrahydrofuran, dioxane, propylene oxide, dimethoxymethane, 1,2-dimethoxyethane, 1,2-diethoxyethane, bis(2-methoxyethyl) ether and bis(2-ethoxyethyl) ether; ketones such as acetone and methyl ethyl ketone; phosphates such as hexamethyl phosphate triamide; amides such as dimethylformamide and dimethylacetoamide; carboxylic acids such as acetic acid and propionic acid; sulfur oxides such as dimethyl sulfoxide and sulfolane.

Among these water-miscible organic solvents, ethanol, isopropanol and acetone are most preferable because of lack of harmful effects to a living body.

A dental primer used in the present kit may comprise, if necessary, a variety of additives such as a polymerization inhibitor, inorganic or organic particles and a dye as a colorant as long as advantages of this invention are not impaired.

A polymerization inhibitor may be added to prevent the primer from gelating during storage, resulting in improvement in its storage stability. Examples of such a polymerization inhibitor include hydroquinone, hydroquinone monomethyl ether and 2,6-di-tert-butylphenol.

Inorganic or organic particles may be added to the primer to adjust a viscosity and fluidity of the primer. Examples of such particles include dry silica, wet silica and polymethyl methacrylate. These particles preferably have a primary particle size of 0.001 µm to 1 µm.

A style of packaging a primer used in the present kit may be appropriately determined, taking storage stability into account. For example, when an easily hydrolyzable component is present, the hydrolyzable component is separated from water or a compound which may act as a catalyst for hydrolysis such as an acid, and they can be combined immediately before use.

In using the present kit, the dental primer is applied on a tooth surface using a sponge or small brush, drying the applied surface, after several seconds to several minutes, by air blowing, then coating the pre-treated tooth surface with a dental adhesive composition of this invention and then applying a variety of restorative materials on the surface.

EXAMPLES

This invention will be concretely described with reference to, but not limited to, examples.

Abbrebiations used in Examples and Comparative Examples have the following meanings.

(1) Acidic-group containing polymerizable monomers, used as component (A) or (D)

PM: a 1:2 (wt/wt) mixture of 2-methacryloyloxyethyl dihydrogenphosphate and bis(2-methacryloyloxyethyl) hydrogenphosphate;

MAC-10: 11-methacryloyloxy-1,1-undecane dicarboxylic acid;

4-META: 4-methacryloyloxyethyl-trimellitic anhydride.

(2) Polymerizable monomers other than an acidic-group containing polymerizable monomer, used as component (A) or (H) Bis-GMA:

2,2,-bis(4-(2-hydroxy-3-methacryloyloxypropoxy)phenyl)propane;

3G: triethyleneglycol dimethacrylate;

D-2.6E: 2,2-bis[(4-methacryloyloxypolyethoxyphenyl)propane];

HEMA: 2-hydroxyethyl methacrylate;

MMA: methyl methacrylate;

TMPT: trimethylol propanetrimethacrylate;

UDMA: a 1:1 (wt/wt) mixture of 1,6-bis(methacrylethyloxycarbonylamino)-2,2,4-trimethylhexane and 1,6-bis(methacrylethyloxycarbonylamino)-2,4,4-trimethylhexane.

(3) Non-crosslinking polymer fillers, used component (B)

PMMA1: non-crosslinking spherical polymethyl methacrylate with an average particle size of 30 µm and a weight average molecular weight of 250,000;

PMMA2: non-crosslinking spherical polymethyl methacrylate with an average particle size of 10 µm and a weight average molecular weight of 500,000;

PMMA3: non-crosslinking spherical polymethyl methacrylate with an average particle size of 10 µm and a weight average molecular weight of 250,000;

PMMA4: non-crosslinking spherical polymethyl methacrylate with an average particle size of 20 µm and a weight average molecular weight of 1,000,000;

PMMA5: non-crosslinking spherical polymethyl methacrylate with an average particle size of 10 µm and a weight average molecular weight of 50,000;

PMMA6: non-crosslinking spherical polymethyl methacrylate with an average particle size of 10 µm and a weight average molecular weight of 15,000;

PEMA1: non-crosslinking spherical polyethyl methacrylate with an average particle size of 10 µm and a weight average molecular weight of 500,000;

PEMA2: non-crosslinking spherical polyethyl methacrylate with an average particle size of 10 µm and a weight average molecular weight of 250,000;

PEMA3: non-crosslinking spherical polyethyl methacrylate with an average particle size of 30 µm and a weight average molecular weight of 250,000.

(4) Polymerization initiators, used as component (C)

BPO: benzoyl peroxide;

DMPT: N,N-dimethyl-p-toluidine;

CQ: camphorquinone;

DMBE: ethyl N,N-dimethyl-p-aminobenzoate.

(5) Aryl borates, used as component (E)

PhBNa: sodium tetraphenylborate;

PhBTEOA: tetraphenylboron triethanolamine salt;

FPhBNa: sodium tetrakis(p-fluorophenyl)borate;

PhBDMPT: tetraphenylboron dimethyl-p-toluidine salt;

PhBDMEM: tetraphenylboron dimethylaminoethyl methacrylate salt;

BFPhBNa: sodium butyltri(p-fluorophenyl)borate.

(6) Organic sulfinic acid salts, used as component (F)

PTSNa: sodium p-toluenesulfinate;

PTSLi: lithium p-toluenesulfinate;

BSNa: sodium benzenesulfinate.

(7) Organic solvents, used as component (I)

IPA: isopropyl alcohol.

Example 1

A dental adhesive composition of this invention comprising 5 wt parts of MAC10, 75 wt parts of MMA and 20 wt parts of HEMA as component (A); 93 wt parts of PMMA1 and 7 wt parts of PEMA1 as component (B); 3 wt parts of DMPT and 2 wt parts of BPO as component (C) was evaluated for a proper-viscosity reaching time, a working time, a curing time and adhesion performance as follows.

(1) Determination of a Proper-viscosity Reaching Time and a Working Time

To a mixing dish was added dropwise 0.103 g of a liquid composition consisting of 5 wt parts of MAC10, 75 wt parts of MMA, 20 wt parts of HEMA and 3 wt parts of DMPT at 23° C. Then, to the mixture was added 0.142 g of powders consisting of 93 wt parts of PMMA1, 7 wt parts of PEMA1 and 2 wt parts of BPO, and the mixture was stirred with a stirring spatula for several seconds at intervals of about 5 sec. A time until the mixture could become to be taken with the spatula (properly viscous state) was measured as a proper-viscosity reaching time. After the proper-viscosity reaching time, the mixture was further stirred and a time until the mixture began to adhere to the spatula as a thread was measured. Thus, a working time was determined as a difference between the latter time and the proper-viscosity reaching time.

(2) Method for Determining a Curing Time

An adhesive composition of this invention was prepared as described in (1). Immediately after reaching a properly viscous state, the mixture was placed in a differential scanning calorimeter (DSC) at 37° C. Measurement was started and a time taken to give the maximum curing heat was measured. A time from the start of measurement to the maximum curing heat was determined as a curing time.

(3) Method for Evaluating Adhesion Performance

Within 24 hours after slaughtering, a bovine front tooth was removed. While pouring water, the tooth was abraded along with a lip surface to expose a dental enamel and a dentin. The exposed tooth surface was dried by blowing it with compressed air for about 10 sec. Then, on the surface was attached a double-stick tape having an opening with a diameter of 3 mm, to form a simulated cavity. In the simulated cavity was applied a proper amount of a dental primer a prepared from 1.7 g of PM, 0.5 g of UDMA, 0.1 g of PhBTEOA, 0.2 g of PTSNa, 4.2 g of acetone and 3.3 g of water. After standing for 30 sec, the applied surface was blown with compressed air for about 5 sec. Then, in the simulated cavity was charged the above dental adhesive composition of this invention in a properly viscous state, on which was then attached a stainless attachment with a diameter of 8 mm φ under pressure to prepare an adhesion test sample.

After immersing the adhesion sample in water at 37° C. for 24 hours, an adhesive strength between the tooth and the attachment was measured using a tensile tester (autograph, Shimadzu Corporation) at a crosshead speed of 1 mm/min.

The measurement results were as follows; a proper-viscosity reaching time: 20 sec, a working time: 100 sec, a curing time: 3.8 min, an adhesive strength to the dental enamel: 23.5 MPa, and an adhesive strength to the dentin: 21.4 MPa, indicating that the dental adhesive composition of this invention exhibits good operability and improved adhesion performance.

Examples 2 to 15

Dental adhesive compositions of this invention were prepared as described in Example 1, except that those shown in Table 1 were used as component (B), and their various properties were evaluated. The results are shown in Table 1, indicating that all of these dental adhesive compositions exhibit good operability and improved adhesion performance.

TABLE 1

| | Non-crosslinking polymer spherical filler(wt parts) | | Proper-viscosity reaching time(s) | Working time(s) | Curing time (min) | Tensile adhesive strength (MPa) | |
|---|---|---|---|---|---|---|---|
| | PMMA spherical filler | PEMA spherical filler | | | | Enamel | Dentin |
| Ex. 1 | PMMA1(93) | PEMA1(7) | 20 | 100 | 3.8 | 23.5 | 21.4 |
| Ex. 2 | PMMA2(95) | PEMA1(5) | 20 | 100 | 3.7 | 24.5 | 20.9 |
| Ex. 3 | PMMA3(93) | PEMA1(7) | 20 | 80 | 3.8 | 22.1 | 20.4 |
| Ex. 4 | PMMA4(90) | PEMA2(10) | 10 | 80 | 3.2 | 19 | 19.4 |
| Ex. 5 | PMMA1(83) + PMMA2(10) | PEMA1(7) | 20 | 100 | 3.8 | 22.9 | 21.2 |
| Ex. 6 | PMMA1(48) + PMMA3(45) | PEMA3(7) | 20 | 110 | 3.9 | 20.4 | 21.6 |
| Ex. 7 | PMMA2(73) + PMMA4(20) | PEMA1(7) | 20 | 100 | 3.6 | 20.1 | 21.3 |
| Ex. 8 | PMMA1(80) + PMMA4(18) | PEMA2(2) | 30 | 120 | 4.1 | 22.5 | 20.9 |
| Ex. 9 | PMMA1(70) + PMMA5(25) | PEMA1(5) | 20 | 110 | 3.6 | 21.4 | 20.6 |
| Ex. 10 | PMMA2(73) + PMMA5(20) | PEMA1(7) | 20 | 70 | 3.2 | 22.8 | 21.5 |
| Ex. 11 | PMMA1(87) + PMMA6(10) | PEMA1(3) | 20 | 120 | 4 | 21.8 | 22 |
| Ex. 12 | PMMA1(35) + PMMA2(40) + PMMA3(20) | PEMA1(5) | 20 | 100 | 3.5 | 20.7 | 21.3 |
| Ex. 13 | PMMA1(43) + PMMA3(40) + PMMA4(10) | PEMA2(7) | 20 | 90 | 3.6 | 21.5 | 20.6 |
| Ex. 14 | PMMA1(20) + PMMA2(23) + PMMA5(50) | PEMA1(7) | 20 | 100 | 3.4 | 21.4 | 22.4 |
| Ex. 15 | PMMA1(43) + PMMA2(30) + PMMA6(20) | PEMA1(3) + PEMA2(4) | 20 | 100 | 3.7 | 22.3 | 19.9 |
| Comp. Ex. 1 | PMMA1(100) | — | 120 | 100 | 5.7 | 21 | 19.9 |
| Comp. Ex. 2 | PMMA1(80) + PMMA3(20) | — | 110 | 110 | 5.6 | 20.7 | 20.7 |
| Comp. Ex. 3 | — | PEMA1(100) | 0 | 10 | 2.6 | 18.9 | 15.3 |

Comparative Example 1

A dental adhesive composition was prepared as described in Example 1, substituting 100 wt parts of PMMA1 alone for component (B) as a non-crosslinking polymer filler, and its various properties were evaluated. The results are shown in Table 1.

In this comparative example, a working time and an adhesive strength were as good as in Example 1, but a proper-viscosity reaching time and a curing time were increased, indicating inadequate operability.

Comparative Examples 2 and 3

Dental adhesive compositions were prepared as described in Example 1, using those shown in Table 1 as a non-crosslinking polymer filler, and its various properties were evaluated. The results are shown in Table 1.

Since a PEMA spherical filler was not used in Comparative Example 2, it is indicated that a proper-viscosity reaching time and a curing time were increased, leading to inadequate operability, as is in Comparative Example 1. In Comparative Example 3 in which a PEMA spherical filler alone was used, a working time was significantly reduced, leading to inadequate operability.

Example 16

A mixed liquid of component (A) consisting of 7.5 g of MMA, 0.5 g of MAC-10 and 2.0 g of HEMA and 0.3 g of DMPT as component (C), and a mixed powder of component (B) consisting of 4.6 g of PMMA1, 4.7 g of PMMA5 and 0.7 g of PEMA1 and 0.2 g of BPO as component (C)

were separately prepared. Immediately before use, the mixed liquid and the mixed powder were kneaded at a powder/liquid ratio (wt/wt) of 1.4, to prepare a dental adhesive composition of this invention. An adhesive strength was determined as described in step (3) in Example 1, using the dental adhesive composition thus prepared. The results were as follows; an adhesive strength to a dental enamel: 23.7 MPa, and an adhesive strength to a dentin: 21.4 MPa. That is, a higher strength was observed for both materials.

Examples 17 to 27

An adhesive strength was determined as described in Example 16, substituting different dental primers having the compositions shown in Table 2 for primer a, in which the primers used in Examples 17 to 27 are referred to as primers b to l, respectively. The results are shown in Table 2. As seen from Table 2, a higher adhesive strength was observed in all Examples.

Example 28

A mixed liquid of component (A) consisting of 7.5 g of MMA, 0.5 g of MAC-10 and 2.0 g of HEMA and 0.3 g of DMPT as component (C), and a mixed powder of component (B) consisting of 9.3 g of PMMA1 and 0.7 g of PMMA1 and 0.2 g of BPO were separately prepared. Immediately before use, the mixed liquid and the mixed powder were kneaded at a powder/liquid ratio of 1.4, to prepare a dental adhesive composition. An adhesive strength was determined as described in Example 16, using the dental adhesive composition thus prepared and the primer a used in Example 16. The results were as follows; an adhesive strength to a dental enamel: 23.4 MPa, and an adhesive strength to a dentin: 22.1 MPa. That is, a higher adhesive strength was observed.

Examples 29 to 51

An adhesive strength was determined as described in Example 16, using different dental primers of this invention

TABLE 2

| | Primer composition(wt parts) | | | | | Tensile adhesive strength(MPa) | |
|---|---|---|---|---|---|---|---|
| | (D) Acidic-group containing polymerizable monomer | (E) Aryl borate | (F) Organo-sulfinic acid salt | (G) Water + (I) Organic solvent | (H) Other polymerizable monomers | Enamel | Dentin |
| Ex. 16 | PM(17) | PhBNa(1) | PTSNa(2) | Water(33) + Acetone(42) | UDMA(5) | 23.7 | 21.4 |
| Ex. 17 | PM(8) | PhBNa(1) | PTSNa(1) | Water(60) | HEMA(30) | 18.5 | 17.9 |
| Ex. 18 | PM(5) | PhBTEOA(0.1) | PTSNa(1) | Water(93.9) | — | 17.2 | 17.1 |
| Ex. 19 | PM(20) | PhBNa(1) | BSNa(1) | Water(40) + Acetone(35) | TMPT(3) | 25.4 | 19.7 |
| Ex. 20 | PM(20) | PhBNa(1) | PTSNa(1) | Water(33) + Acetone(36) + IPA(4) | UDMA(5) | 23.7 | 22.7 |
| Ex. 21 | MAC-10(5) + PM(15) | PhBTEOA(1) | PTSNa(3) | Water(36) + Acetone(25) + IPA(10) | D-2.6E(5) | 21.1 | 18.9 |
| Ex. 22 | MAC-10(10) + PM(10) | FPhBNa(3) | BSNa(5) | Water(35) + Acetone(27) | UDMA(10) | 20.8 | 21.5 |
| Ex. 23 | 4-META(10) + PM(10) | PhBDPT(5) | PTSLi(1) | Water(41) + Acetone(23) | UDMA(5) + D-2.6E(5) | 23.6 | 19.8 |
| Ex. 24 | MAC-10(10) + PM(15) | PhBDMEM(2) | PTSNa(0.3) | Water(25) + Acetone(42.7) | Bis-GMA(3) + 3G(2) | 22.6 | 19.3 |
| Ex. 25 | PM(20) | BFPhBNa(0.5) | PTSNa(1) + BSNa(1) | Water(39.5) + Acetone(20) | UDMA(5) + HMA(5) | 24.6 | 18.9 |
| Ex. 26 | PM(20) | PhBNa(1) | PTSNa(2) | Water(37) + Acetone(35) | UDMA(3) + 3G(2) | 22.2 | 20.5 |
| Ex. 27 | 4-META(10) + MAC-10(10) | PhBNa(1) + PhBTEOA(1) | PTSNa(1) | Water(37) + Acetone(35) | UDMA(3) + TMPT(2) | 18.3 | 21.4 |
| Comp. Ex. 4 | — | PhBNa(1) | PTSNa(1) | Water(48) + Acetone(45) | UDMA(5) | 0.6 | 3.6 |
| Comp. Ex. 5 | PM(20) | — | PTSNa(1) | Water(39) + Acetone(35) | UDMA(5) | 15.4 | 12.1 |
| Comp. Ex. 6 | PM(20) | PhBNa(1) | — | Water(39) + Acetone(35) | UDMA(5) | 16.4 | 13.4 |
| Comp. Ex. 7 | PM(20) | PhBNa(1) | PTSNa(1) | — | UDMA(78) | — | — |

Comparative Examples 4 to 7

An adhesive strength was determined as described in Example 16, using different dental primers having the compositions shown in Table 2, in which the primers used in Comparative Examples 4 to 7 are referred to as primers m to p, respectively. The results are shown in Table 2.

In Comparative Example 4, in which an acidic-group containing polymerizable monomer was not contained in the primer, adhesive strength values to a dental enamel and a dentin were as low as 0.6 MPa and 3.6 MPa, respectively. In Comparative Example 5, in which an aryl borate was not contained in the primer, an adhesive strength to a dentin was significantly lowered. In Comparative Example 6 without an organosulfinic acid salt, an adhesive strength to a dentin was significantly lowered. In Comparative Example 7 without water or a solvent, a homogeneous solution failed to be prepared because PTSNa as an organosulfinic acid salt was not dissolved in PM and UDMA and the primer failed to exhibit a proper viscosity. Thus, an adhesion test could not be conducted.

having the compositions shown in Tables 3 and 4, and different primers (primers a, e and k). However, when adding a photopolymerization initiator to component (C), further an attachment was welded under a pressure and then irradiation was conducted from four directions around the attachment for 30 sec for each direction. The results are shown in Tables 3 and 4. In all Examples, higher adhesive strength was observed to both dental enamel and dentin.

TABLE 3

Composition of dental adhesive compositions(wt parts)

| | | Polymerizable monomer comprising an acidic-group containign ploymerizable monomer | | | | | | | | Non-crosslinking spherical filler | | Polymeriza-tion initiator | | Tensile adhesive strength(MPa) | |
|---|---|---|---|---|---|---|---|---|---|---|---|---|---|---|---|
| | | Acidic group containing polymerizable monomer | | Other polymerizable monomers | | | | | | | PMMA spherical filler | | | | |
| Pri-mer | | PMA | MAC-10 | 4-META | MMA | HEMA | D-26E | Bis-GMA | UD3G | PMMA | PMMA spherical filler | | BPO | DMPT | Enamel | Dentin |
| Ex. 28 | a | — | 5 | — | 75 | 20 | — | — | — | — | PMMA1(130.2) | PEMA1(9.8) | 2.8 | 3 | 23.4 | 22.1 |
| Ex. 29 | a | — | 5 | — | 75 | 20 | — | — | — | — | PMMA1(102.2) + PMMA2(28) | PEMA1(9.8) | 2.45 | 3 | 23.1 | 21.8 |
| Ex. 30 | a | — | — | 5 | 75 | 20 | — | — | — | — | PMMA1(105) + PMMA3(28) | PEMA1(7) | 2.8 | 3 | 24.5 | 20.8 |
| Ex. 31 | a | 5 | — | — | 75 | 20 | — | — | — | — | PMMA1(120.2) + PMMA4(10) | PEMA1(9.8) | 2.1 | 3 | 20.7 | 19.9 |
| Ex. 32 | e | — | 3 | — | 77 | 20 | — | — | — | — | PMMA2(105) + PMMA3(28) | PEMA1(7) | 2.8 | 3 | 21.1 | 19.7 |
| Ex. 33 | e | — | 10 | — | 70 | 20 | — | — | — | — | PMMA1(116.2) + PMMA5(14) | PEMA1(9.8) | 2.8 | 5 | 22.2 | 19.7 |
| Ex. 34 | e | — | 20 | — | 70 | 10 | — | — | — | — | PMMA1(112) + PMMA5(23.8) | PEMA1(4.2) | 2.8 | 3 | 20.8 | 17.9 |
| Ex. 35 | e | 5 | 5 | — | 60 | 20 | 10 | — | — | — | PMMA4(70) + PMMA5(63) | PEMA1(7) | 2.1 | 3 | 21.4 | 20.4 |
| Ex. 36 | k | — | 5 | 5 | 65 | 20 | — | 5 | — | — | PMMA1(105) + PMMA3(28) | PEMA2(7) | 1.4 | 2 | 22.3 | 21.1 |
| Ex. 37 | k | — | 5 | — | 70 | 15 | — | — | 6 | 4 | PMMA1(70.2) + PMMA5(60) | PEMA2(9.8) | 2.8 | 3 | 21.6 | 20.6 |
| Ex. 38 | k | — | 5 | — | 65 | 20 | — | — | — | 10 | PMMA2(105) + PMMA3(28) | PEMA3(7) | 2.45 | 3 | 21 | 19.8 |
| Ex. 39 | k | — | 10 | — | 65 | 15 | 10 | — | — | — | PMMA3(109.2) + PMMA(28) | PEMA3(2.8) | 2.1 | 3 | 20.8 | 20.5 |

TABLE 4

Composition of dental adhesive compositions(wt parts)

| | | Polymerizable monomer comprising an acidic-group containing polymerizable monomer | | | | | | Non-crosslinking spherical filler | | Polymerization initiator | | | | | Tensile adhesive strength(MPa) | |
|---|---|---|---|---|---|---|---|---|---|---|---|---|---|---|---|---|
| | | Acidic group containing polymerizable monomer | | Other polymerizable monomers | | | | | PEMA spherical filler | | | | | | | |
| | Pri-mer | MAC-10 | 4-META | MMA | HEMA | D-2.6E | TMPT | PMMA spherical filler | | BPO | DMPT | CQ | DMBE | PhBNa | Enamel | Dentin |
| Ex. 40 | a | 5 | — | 75 | 20 | — | — | PMMA1(105.2) + PMMA2(25) | PEMA1(9.8) | 2.8 | 3 | 2 | 2 | — | 24.7 | 23.4 |
| Ex. 41 | a | 5 | — | 75 | 20 | — | — | PMMA3(70.2) + PMMA4(60) | PEMA1(9.8) | 2.8 | 3 | — | — | 2 | 23.1 | 22.2 |
| Ex. 42 | a | 5 | — | 75 | 20 | — | — | PMMA1(105) + PMMA5(28) | PEMA1(7) | 2.8 | 3 | 2 | 2 | 1 | 24 | 20.8 |
| Ex. 43 | a | 5 | 5 | 70 | 20 | — | — | PMMA3(112) + PMMA5(25.2) | PEMA1(2.8) | 2.1 | 3 | — | — | — | 24 | 22.7 |
| Ex. 44 | e | 5 | — | 65 | 20 | 10 | — | PMMA1(52) + PMMA2(52) + PMMA3(29) | PEMA1(7) | 2.8 | 3 | — | — | — | 25.1 | 22.5 |
| Ex. 45 | e | 10 | — | 65 | 15 | 10 | — | PMMA1(50) + PMMA3(50) + PMMA5(30.2) | PEMA2(9.8) | 2.8 | 3 | 2 | 2 | — | 21.6 | 23 |
| Ex. 46 | e | 5 | — | 75 | 15 | — | 5 | PMMA1(50) + PMMA3(50) + PMMA4(33) | PEMA1(7) | 2.8 | 3 | — | — | 1 | 21 | 22.4 |

TABLE 4-continued

Composition of dental adhesive compositions(wt parts)

| | Primer | Polymerizable monomer comprising an acidic-group containing polymerizable monomer | | | | | | Non-crosslinking spherical filler | | Polymerization initiator | | | | | Tensile adhesive strength(MPa) | |
| | | Acidic group containing polymerizable monomer | | Other polymerizable monomers | | | | | PEMA spherical filler | | | | | | | |
| | | MA C-10 | 4-ME TA | M MA | HE MA | D-2 .6E | TM PT | PMMA spherical filler | | BPO | DM PT | CQ | DM BE | PhB Na | Enamel | Dentin |
|---|---|---|---|---|---|---|---|---|---|---|---|---|---|---|---|---|
| Ex. 47 | e | — | 5 | 70 | 20 | — | 5 | PMMA1(60.2) + PMMA3(42) + PMMA6(28) | PEMA2(9.8) | 2.1 | 3 | — | — | — | 21.1 | 23.5 |
| Ex. 48 | k | 5 | — | 75 | 20 | — | — | PMMA1(32) + PMMA2(32) + PMMA5(69) | PEMA1(7) | 2.45 | 2 | — | — | — | 20.8 | 21.9 |
| Ex. 49 | k | 5 | — | 75 | 20 | — | — | PMMA1(30) + PMMA2(30) + PMMA6(70.2) | PEMA1(9.8) | 2.8 | 2 | — | — | — | 23.1 | 22.7 |
| Ex. 50 | k | 10 | — | 70 | 20 | — | — | PMMA1(105) + PMMA3(28) | PEMA1(4) + PEMA2(3) | 2.45 | 3 | — | — | 1 | 21.5 | 22.5 |
| Ex. 51 | k | 5 | — | 75 | 10 | 10 | — | PMMA1(50) + PMMA3(50) + PMMA5(33) | PEMA1(4) + PEMA3(3) | 2.45 | 3 | — | — | — | 21.9 | 23.5 |
| Comp. Ex. 8 | a | — | — | — | — | — | — | PMMA1(105) + PMMA2(28) | PEMA1(7) | 2.8 | 3 | — | — | — | — | — |
| Comp. Ex. 9 | a | — | — | 70 | 20 | 10 | — | PMMA1(105) + PMMA3(28) | PEMA1(7) | 2.8 | 3 | — | — | — | 0.5 | 3.4 |
| Comp. Ex. 10 | e | 5 | — | 65 | 20 | 10 | — | — | — | 2.8 | 3 | — | — | — | — | — |
| Comp. Ex. 11 | e | 5 | — | 65 | 20 | 10 | — | PMMA1(105) + PMMA3(28) | PEMA1(7) | — | — | — | — | — | — | — |

Comparative Examples 8 to 11

An adhesive strength was determined as described in Examples 29 to 51, using dental adhesive compositions having the compositions and the primers shown in Table 4. The results are shown in Table 4.

Comparative Example 8 is an example which is without an acidic-group containing polymerizable monomers or other polymerizable monomers as component (A) in an adhesive composition, an adhesion test could not be conducted.

Comparative Example 9 is an example which is without an acidic-group containing polymerizable monomer in an adhesive composition, adhesive strength to a dental enamel and dentin was significantly lowered. Comparative Example 10 is an example which is without a non-crosslinking polymer filler in an adhesive composition, the composition did not have a proper viscosity so that an adhesion test could not be conducted. Comparative Example 11 is an example which is without a polymerization catalyst, the composition failed to be polymerized so that an adhesion test could not be conducted.

What is claimed is:

1. A dental adhesive composition comprising (A) a polymerizable monomer comprising an acidic-group containing polymerizable monomer; (B) a spherical filler substantially consisting of a non-crosslinking polymethyl methacrylate and a spherical filler substantially consisting of a non-crosslinking polyethyl methacrylate; and (C) a polymerization initiator.

2. The dental adhesive composition as claimed in claim 1 wherein a content of (A) the polymerizable monomer comprising an acidic-group containing polymerizable monomer is 25 to 65 wt parts to 100 parts of the total amount of (A) the polymerizable monomer comprising an acidic-group containing polymerizable monomer, (B) the spherical filler substantially consisting of a non-crosslinking polymethyl methacrylate and the spherical filler substantially consisting of a non-crosslinking polyethyl methacrylate and (C) the polymerization initiator; a content of (B) the spherical filler substantially consisting of a non-crosslinking polymethyl methacrylate and the spherical filler substantially consisting of a non-crosslinking polyethyl methacrylate is 35 to 70 wt parts to 100 wt parts of the total amount of (A) the polymerizable monomer comprising an acidic-group containing polymerizable monomer, (B) the spherical filler substantially consisting of a non-crosslinking polymethyl methacrylate and the spherical filler substantially consisting of a non-crosslinking polyethyl methacrylate and (C) the polymerization initiator; a content of (C) the polymerization initiator is 0.01 to 20 wt parts to 100 parts of (A) the polymerizable monomer comprising an acidic-group containing polymerizable monomer.

3. The dental adhesive composition as claimed in claim 1 wherein a content of the acidic-group containing polymerizable monomer is 3 to 70 wt parts of (A) the polymerizable monomer comprising the acidic-group containing polymerizable monomer.

4. The dental adhesive composition as claimed in claim 1 wherein (A) the polymerizable monomer comprising an acidic-group containing polymerizable monomer comprises 11-methacryloyloxy-1,1-undecane dicarboxylic acid.

5. The dental adhesive composition as claimed in claim 1 wherein (A) the polymerizable monomer comprising an acidic-group containing polymerizable monomer comprises a polymerizable monomer having a functional group including a thiouracil, triazinethione or mercaptothiazole derivative at 0.1 to 50 wt parts to 100 wt parts of (A) the polymerizable monomer comprising an acidic-group containing polymerizable monomer.

6. The dental adhesive composition as claimed in claim 1 wherein an average particle size of (B) the spherical filler substantially consisting of a non-crosslinking polymethyl methacrylate and the spherical filler substantially consisting of a non-crosslinking polyethyl methacrylate is 0.1 to 50 $\mu$m.

7. The dental adhesive composition as claimed in claim 1 wherein the spherical filler substantially consisting of a non-crosslinking polymethyl methacrylate in (B) is a mixture of a spherical filler having a weight average molecular weight of less than 100,000 and a spherical filler having a weight average molecular weight of 100,000 or more.

8. A dental adhesion kit comprising the dental adhesive composition as claimed in claim 1 in combination with a dental primer comprising (D) an acidic-group containing polymerizable monomer, (E) an aryl borate, (F) an organosulfinic acid salt and (G) water.

9. The dental adhesion kit as claimed in claim 8 wherein a content of (D) the acidic-group containing polymerizable monomer in the primer is 1 to 50 wt parts to 100 parts of the total of the components of the primer; a content of (E) the aryl borate is 0.01 to 25 wt parts to 100 parts of the total of polymerizable monomer of the primer; a content of (F) the organosulfinic acid salt is 0.01 to 25 wt parts to 100 parts of the total of polymerizable monomer of the primer; and a content of (G) water is 5 to 95 wt parts to 100 parts of the total of the components of the primer.

10. The dental adhesion kit as claimed in claim 8 wherein (E) the aryl borate has three or four aryl groups in one molecule.

11. A dental adhesion kit comprising the dental adhesive composition as claimed in claim 1 in combination with a dental primer comprising (D) an acidic-group containing polymerizable monomer, (E) an aryl borate, (F) an organosulfinic acid salt, (G) water, (H) a polymerizable monomer other than the acidic-group containing polymerizable monomer and (I) an organic solvent.

* * * * *